United States Patent
Davis et al.

(10) Patent No.: US 9,585,915 B2
(45) Date of Patent: Mar. 7, 2017

(54) POLYPEPTIDE HYDROGELS AND USES RELATED THERETO

(71) Applicants: EMORY UNIVERSITY, Atlanta, GA (US); GEORGIA TECH RESEARCH CORPORATION, Atlanta, GA (US)

(72) Inventors: Michael E. Davis, Atlanta, GA (US); Archana V. Boopathy, Lilburn, GA (US)

(73) Assignees: Emory University, Atlanta, GA (US); Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 14/602,839

(22) Filed: Jan. 22, 2015

(65) Prior Publication Data

US 2015/0216906 A1 Aug. 6, 2015

Related U.S. Application Data

(60) Provisional application No. 61/930,713, filed on Jan. 23, 2014.

(51) Int. Cl.
| | |
|---|---|
| *C07K 16/00* | (2006.01) |
| *A61K 35/34* | (2015.01) |
| *C12N 5/077* | (2010.01) |
| *C07K 14/00* | (2006.01) |
| *C07K 14/705* | (2006.01) |
| *C12N 5/00* | (2006.01) |

(52) U.S. Cl.
CPC .............. *A61K 35/34* (2013.01); *C07K 14/00* (2013.01); *C07K 14/70596* (2013.01); *C12N 5/0068* (2013.01); *C12N 5/0657* (2013.01); *C07K 2319/70* (2013.01); *C07K 2319/75* (2013.01); *C12N 2501/42* (2013.01)

(58) Field of Classification Search
None
See application file for complete search history.

(56) References Cited

U.S. PATENT DOCUMENTS

| | | | |
|---|---|---|---|
| 7,399,831 B2 | 7/2008 | Lee | |
| 7,887,796 B2* | 2/2011 | Itescu | A61K 38/2053 424/130.1 |
| 8,299,032 B2 | 10/2012 | Yokoi | |
| 8,722,850 B2 | 5/2014 | Vescovi | |
| 2006/0177479 A1* | 8/2006 | Giachelli | A61K 38/17 424/426 |
| 2012/0010140 A1 | 1/2012 | Ellis-Behnke | |
| 2012/0014925 A1* | 1/2012 | Kumada | A61L 27/227 424/93.7 |
| 2012/0207705 A1* | 8/2012 | Kara | A61K 38/1709 424/85.2 |

OTHER PUBLICATIONS

Ramanjuan et al. TRENDS in Biochemical Sciences. vol. 31 No. 10, 2006.*
Banta et al. "Protein Engineering in the Development of Functional Hydrogels" Annu. Rev. Biomed. Eng., 2010; 12: 167-186.
Beltrami et al. "Adult Cardiac Stem Cells Are Multipotent and Support Myocardial Regeneration" Cell, 2003; 114: 763-776.
Boni et al. "Notch1 regulates the fate of cardiac progenitor cells" PNAS, Oct. 7, 2008; 105(40): 15529-15534.
Boopathy et al. poster on Jul. 24, 2013 at Basic Cardiovascular Science (BCVS) meeting in Las Vegas.
Boopathy et al. "The modulation of cardiac progenitor cell function by hydrogel dependent Notch1activation" Biomaterials, 2014; 35(28): 8103-8112.
Boopathy et al. "Intramyocardial Delivery of Notch Ligand-Containing Hydrogels Improves Cardiac Function and Angiogenesis Following Infarction" Tissue Engineering: Part A, 2015; 21(17-18): 2315-2322.
Davis et al. "Local myocardial insulin-like growth factor 1 (IGF-1) delivery with biotinylated peptide nanofibers improves cell therapy for myocardial infarction" PNAS, May 23, 2006; 103(21): 8155-8160.
Kisiday et al. "Self-assembling peptide hydrogel fosters chondrocyte extracellular matrix production and cell division: Implications for cartilage tissue repair" PNAS, Jul. 23, 2002; 99(15): 9996-10001.
Kopan et al. "The Canonical Notch Signaling Pathway: Unfolding the Activation Mechanism" Cell, Apr. 17, 2009; 137: 216-233.
Kyle et al. "Production of self-assembling biomaterials for tissue engineering" Trends in Biotechnology, 2009; 27(7): 423-433.
Leri et al. "Role of Cardiac Stem Cells in Cardiac Pathophysiology: A Paradigm Shift in Human Myocardial Biology" Circ Res., Sep. 30, 2011; 109(8): 941-961.
Levit et al. "Cellular Encapsulation Enhances Cardiac Repair" J Am Heart Assoc., 2013; 2: e000367.
Nickoloff et al. "Jagged-1 mediated activation of notch signaling induces complete maturation of human keratinocytes through NF-kB and PPARgama" Cell Death and Differentiation, 2002; 9: 842-855.
Niessen et al. "Notch Signaling in Cardiac Development" Circ Res., 2008; 102: 1169-1181.
Padin-Iruegas et al. "Cardiac Progenitor Cells and Biotinylated Insulin-Like Growth Factor-1 Nanofibers Improve Endogenous and Exogenous Myocardial Regeneration After Infarction" Circulation, 2009; 120: 876-887.

(Continued)

*Primary Examiner* — Jeanette Lieb
(74) *Attorney, Agent, or Firm* — Emory Patent Group

(57) ABSTRACT

This disclosure relates to self-assembling peptides that form hydrogels comprising peptide sequences for the activation of signaling pathways. In certain embodiments, the disclosure relates to compositions comprising a recombinant polypeptide comprising a cell signaling sequence, e.g., JAG-1 sequence, fused to a hydrogel polypeptide sequence. In certain embodiments, the disclosure relates to methods of cell culture on three dimensional scaffolds/hydrogels composed of self-assembling peptides disclosed herein.

4 Claims, 9 Drawing Sheets

(56) References Cited

OTHER PUBLICATIONS

Raya et al. "Activation of Notch signaling pathway precedes heart regeneration in zebrafish" PNAS, Sep. 30, 2003: 100(suppl. 1): 11889-11895.
Segers et al. "Local delivery of proteins and the use of self-assembling peptides" Drug Discovery Today, Jul. 2007; 12(13/14): 561-568.

* cited by examiner

SEQUENCE LISTING

```
<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<223> OTHER INFORMATION: Synthetic constructs

<400> SEQUENCE: 1

Cys Asp Asp Tyr Tyr Tyr Gly Phe Gly Cys Asn Lys Phe Cys Arg Pro
1               5                   10                  15

Arg

<210> SEQ ID NO 2
<211> LENGTH: 16
<212> TYPE: PRT
<213> ORGANISM: Artificial Sequence
<220> FEATURE:
<223> OTHER INFORMATION: Synthetic constructs

<400> SEQUENCE: 2

Arg Ala Arg Ala Asp Ala Asp Ala Arg Ala Arg Ala Asp Ala Asp Ala
1               5                   10                  15

<210> SEQ ID NO 3
<211> LENGTH: 8
```

```
<212> TYPE: PRT
<213> ORGANISM: Artificial Sequence
<220> FEATURE:
<223> OTHER INFORMATION: Synthetic constructs

<400> SEQUENCE: 3

Arg Ala Arg Ala Asp Ala Asp Ala
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic constructs

<400> SEQUENCE: 4

Arg Cys Gly Pro Asp Cys Phe Asp Asn Tyr Gly Arg Tyr Lys Tyr Cys
1               5                   10                  15

Phe

<210> SEQ ID NO 5
<211> LENGTH: 40
<212> TYPE: PRT
<213> ORGANISM: Artificial Sequence
<220> FEATURE:
<223> OTHER INFORMATION: Synthetic constructs

<400> SEQUENCE: 5

Arg Ala Arg Ala Asp Ala Asp Ala Arg Ala Arg Ala Asp Ala Asp Ala
1               5                   10                  15

Gly Gly Gly Gly Gly Gly Cys Asp Asp Tyr Tyr Tyr Gly Phe Gly
            20                  25                  30

Cys Asn Lys Phe Cys Arg Pro Arg
        35                  40

<210> SEQ ID NO 6
<211> LENGTH: 40
<212> TYPE: PRT
<213> ORGANISM: Artificial Sequence
<220> FEATURE:
<223> OTHER INFORMATION: Synthetic Constructs

<400> SEQUENCE: 6

Arg Ala Arg Ala Asp Ala Asp Ala Arg Ala Arg Ala Asp Ala Asp Ala
1               5                   10                  15

Gly Gly Gly Gly Gly Gly Gly Arg Cys Gly Pro Asp Cys Phe Asp Asn
            20                  25                  30

Tyr Gly Arg Tyr Lys Tyr Cys Phe
        35                  40
```

POLYPEPTIDE HYDROGELS AND USES RELATED THERETO

CROSS-REFERENCE TO RELATED APPLICATIONS

This Application claims the benefit of priority to U.S. Provisional Application No. 61/930,713 filed Jan. 23, 2014, hereby incorporated by reference in its entirety.

STATEMENT REGARDING FEDERALLY SPONSORED RESEARCH

This invention was made with government support under contract numbers HHSN268201000043C, R01-GM097399, and DP3DK094346 awarded National Institutes of Health. The government has certain rights in the invention.

BACKGROUND

Cardiovascular disease is a leading cause of mortality. Although many therapies attempt to improve functionality of the heart, for chronic heart failure, cardiac transplantation is typically the only long term option. Owing to low availability of donor hearts, improved treatments are needed. Administering bone-marrow-derived mesenchymal stem cells (MSCs) has beneficial effects for a patient that have experienced a myocardial infarction (MI), and human clinical trials demonstrated modest, yet significant, improvements in cardiac performance. However, cell therapy for heart failure is limited by the lack of implanted cell retention in the infarcted heart. Thus, there is a need for improvement.

Kisiday et al. report a self-assembling peptide hydrogel fosters chondrocyte extracellular matrix production and cell division. PNAS, 2002, 99(15):9996-10001. Davis et al. report local myocardial insulin-like growth factor 1(IGF-1) delivery with biotinylated peptide nanofibers improves cell therapy for myocardial infarction. PNAS, 2006, 103, 8155-8160. Padin-Iruegas et al. report cardiac progenitor cells and biotinylated insulin-like growth factor-1 nanofibers improve endogenous and exogenous myocardial regeneration after infarction. Circulation, 2009, 120, 876-887. Kyle et al., report the production of self-assembling biomaterials for tissue engineering. Trends Biotechnol, 2009, 27(7):423-33. See also Segers & Lee, Drug Discovery Today, 2007, 12, 561-568, U.S. Pat. Nos. 7,399,831, and 8,299,032, and US Published Application Numbers 2013/0053324 and 2012/0010140.

Notch signaling is an evolutionarily conserved intercellular communication pathway that regulates diverse cellular processes, ranging from cell-fate decision, differentiation, and proliferation to apoptosis. See Kopan et al., Cell, 2009, 137: 216-33. Activation of the Notch receptor by adjacent cell surface-bound ligands of the Jagged and Delta family leads to proteolytic cleavage and nuclear translocation of the Notch intracellular domain (NICD). Apart from regulating normal development and damage-induced repair, Notch signaling has also been found to promote cardiomyocyte survival. Notch activation promotes cardiac gene expression in circulating endothelial progenitor cells, bone-marrow derived MSCs, and cardiac progenitors. See Niessen & Karsan, Circ Res, 2008, 4:1169-1181; Raya et al., PNAS, 2003, 4:11889-11895; Beltrami et al., Cell, 2003, 4:763-776; and Boni et al., PNAS, 2008, 4:15529-15534. Nickoloff et al., report Jagged-1 mediated activation of Notch signaling induces complete maturation of human keratinocytes through NF-kappaB and PPARgamma. Cell Death Differ, 2002, 9(8):842-55.

Boopathy et al. report the modulation of cardiac progenitor cell function by hydrogel-dependent Notch1 activation. Biomaterials, 2014, 35(28):8103-12. Boopathy & Davis report self-assembling peptide-based delivery of therapeutics for myocardial infarction. Methods Mol Biol, 2014, 1141:159-64. Levit et al. report cellular encapsulation enhances cardiac repair. J Am Heart Assoc, 2013, 2(5): e000367.

References cited herein are not an admission of prior art.

SUMMARY

This disclosure relates to self-assembling peptides that form hydrogels comprising peptide sequences for the activation of signaling pathways. In certain embodiments, the disclosure relates to compositions comprising a recombinant polypeptide comprising a cell signaling sequence, e.g., JAG-1 sequence, fused to a hydrogel polypeptide sequence. In certain embodiments, the disclosure relates to methods of cell culture on three dimensional scaffolds/hydrogels composed of self-assembling peptides disclosed herein.

In certain embodiments, hydrogels disclosed herein comprise cells, optionally the cells may be allowed to replicate, and optionally one may implant the hydrogel, cells, or both the hydrogel and cells into area of a subject. Typically, the peptide sequence activates signaling of pathways producing a desired effect, e.g., improving the growth or replication of tissue or cells producing cells and tissues with desired characteristics.

In certain embodiments, the disclosure relates to recombinant polypeptides comprising a JAG-1 sequence sufficient to activate Notch1 signaling fused to a hydrogel polypeptide sequence and compositions comprising the recombinant polypeptides. In certain embodiments, the disclosure relates to recombinant nucleic acids encoding recombinant polypeptides disclosed herein. In certain embodiments, the disclosure relates to vectors comprising recombinant nucleic acids disclosed herein. In certain embodiments, the disclosure relates to expression systems comprising vectors and nucleic acids disclosed herein configured to produce recombinant polypeptides disclosed herein.

In certain embodiments, the JAG-1 sequence is CDDYYYGFGCNKFCRPR (SEQ ID NO: 1) or variant thereof. In certain embodiments, the variant has greater than 40%, 50%, 60%, 70%, 80%, or 90% sequence identity or similarity thereto. In certain embodiments, the variant comprises one, two, three, four, or five amino acid substitutions. In certain embodiments, the variant comprises conserved amino acid substitutions. In certain embodiments, the variant comprises one, two, three, four, or five amino acid deletions.

In certain embodiments, the hydrogel polypeptide sequence comprises greater than about 40%, 50%, or 60% hydrophilic amino acids. In certain embodiments, the hydrogel polypeptide sequence comprises six, eight, ten, twelve, fourteen, sixteen or greater alternating hydrophobic and hydrophilic amino acids. In certain embodiments, hydrophilic amino acid has a side chain comprising carboxylic acid group or hydroxyl group. In certain embodiments, hydrophobic amino acid has an aliphatic side chain. In certain embodiments, the hydrogel polypeptide sequence is RARADADARARADADA (SEQ ID NO: 2) or variant thereof. In certain embodiments, the variant has greater than 40%, 50%, 60%, 70%, 80%, or 90% sequence identity or similarity thereto. In certain embodiments, the variant comprises one, two, three, four, or five, amino acid substitutions. In certain embodiments, the variant comprises conserved amino acid substitutions. In certain embodiments, the variant comprises one, two, three, four, or five, amino acid deletions.

In certain embodiments, the disclosure relates to recombinant polypeptides comprising a JAG-1 sequence fused to a hydrogel sequence wherein the JAG-1 sequence fused to the hydrogel sequence through a polypeptide linker. In certain embodiments, the disclosure relates to a recombinant polypeptide comprising CDDYYYGFGCNKFCRPR (SEQ ID NO: 1) or variant thereof and RARADADA (SEQ ID NO: 3) repeats or variant thereof. In certain embodiments, the linker is polyglycine of greater than 2, 3, 4, 5, 6, 7, 8, 9, 10, 11, 12, 13, 14, 15, 16, 17, 18, 19, 20, or 25 glycine amino acids, or between 2 to 12, or 5 to 8 glycine amino acids.

In certain embodiments, the disclosure relates to hydrogels comprising recombinant polypeptides disclosed herein. In certain embodiments, the hydrogel further comprises a hydrogel polypeptide sequence in combination with a recombinant polypeptide disclosed herein.

In certain embodiments, the hydrogel polypeptide sequence and the recombinant polypeptide are in a ratio of between 1:1 to 1:100, or 1:2 to 1:50, or 1:3 to 1:25, or 1:4 to 1:20, or 1:5 to 1:15 by weight. In certain embodiments, the polypeptides are about 1% or about 2% or between 0.5% to 1.5%, or 1.5% to 2.5%, or 0.5% to 3%, or 0.5% to 5.0%, or 0.1 to 10%, or 0.01% to 20%, by weight to volume of the hydrogel.

In certain embodiments, the hydrogel further comprises a saccharide at a concentration of between 10 mM to 1000 mM or 100 mM to 500 mM. In certain embodiments, the hydrogel further comprises a buffer creating a pH of between 5.0 to 10.0, or 6.5 to 8.5, or 7.0 to 7.7.

In certain embodiments, the disclosure relates to methods of growing cells comprising placing an isolated cell on or in a hydrogel disclosed herein under conditions such that the cell replicates. In certain embodiments, the isolated cell is a stem cell, progenitor cell, cardiac stem cell, cardiac progenitor cell, bone marrow derived cell, or mesenchymal stem cell. In certain embodiments, the cell is isolated by biopsy of cardiac tissue of by the process of selecting cells for stem cell surface markers, progenitor cell surface markers, or cardiac cell surface markers.

In certain embodiments, the disclosure relates to hydrogels prepared from the self-assembling peptides disclosed herein further comprising cells, e.g., stem or progenitor cell preparations or cardiac cells, inside or on the surface of the hydrogels.

In certain embodiments, the disclosure relates to methods of treating or preventing cardiovascular disease or disorder comprising administering an effective amount of a composition comprising cells grown by the processes disclosed herein to a subject in need thereof. In certain embodiments, the composition is administered by injection into cardiac tissue or pericardium, and/or infusion into the circulatory system. In certain embodiments, the composition is administered by implanting a hydrogel disclosed herein in an area of the subject, e.g. within or adjacent to cardiac tissue or cells.

In certain embodiments, the cells are autologous. In certain embodiments, the disclosure relates to methods of treating or preventing cardiovascular disease or disorder comprising isolating cells from a subject, contacting the cells with a hydrogel disclosed herein, optionally replicating the cells, optionally altering the cells by genetic engineering, and administering the cells back into the subject or implanting the hydrogel into a desired area of the subject.

In certain embodiments, the disclosure relates to compositions made by processes disclosed herein. In certain embodiments, the disclosure relates to mixing cells and hydrogels disclosed herein under conditions such that cells with desirable characteristic are formed.

DETAILED DISCUSSION

Figure 1A:
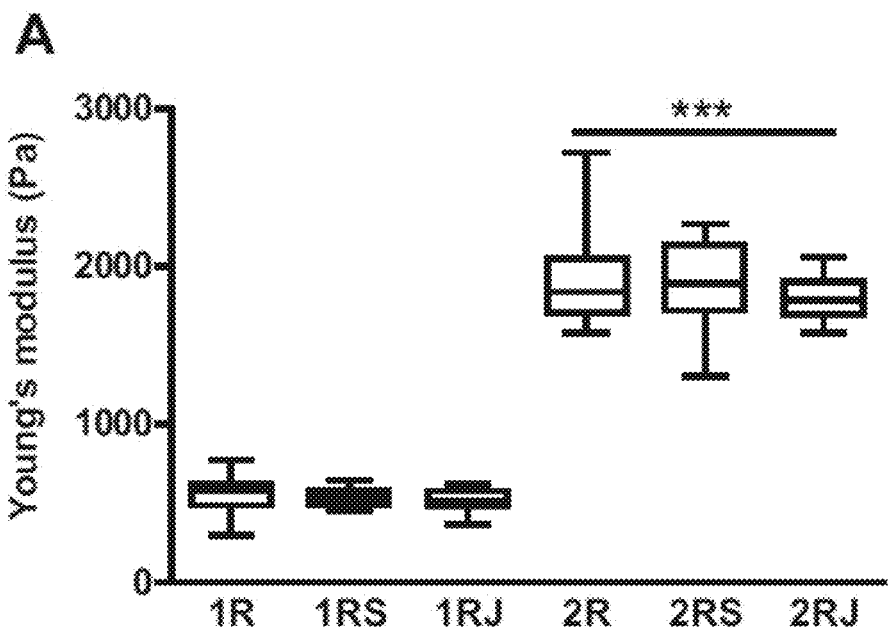
FIG. 1A shows data on the mechanical characterization of hydrogels using atomic Force Microscopy measurements of Young's modulus of hydrogels. The average Young's modulus of the 1% hydrogels (1R, 1RS and 1RJ) is 500 Pa and the 2% hydrogels (2R, 2RS, 2RJ) is 1800 Pa.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, and the like, which are within the skill of the art. Such techniques are explained fully in the literature.

In this specification and in the claims that follow, reference will be made to a number of terms that shall be defined to have the following meanings unless a contrary intention is apparent.

It must be noted that, as used in the specification and the appended claims, the singular forms "a," "an," and "the" include plural referents unless the context clearly dictates otherwise.

A "gel" refers to a nonfluid colloidal network or polymer network that is expanded throughout its volume by a fluid. The polymer network may be a covalent polymer network, e.g., a network formed by crosslinking polymer chains by nonlinear polymerization. The colloidal network may be a polymer network formed through the physical aggregation of polymer chains, caused by hydrogen bonds, crystallization, helix formation, complexation, or other manner that results in regions of local order. The polymers may be globular or fibrillar proteins.

The term "hydrogel" refers to gel containing network integrated with water. Typically, water is greater than half of the gel by weight, and typically greater than 80%, 90%, 95% or more by weight. A "hydrogel polypeptide" refers to hydrophilic polypeptides capable of producing hydrogels. Kisiday et al. report a self-assembling peptide hydrogel fosters chondrocyte extracellular matrix production and cell division. Proc Natl Acad Sci U S A, 2002, 99(15):9996-10001. Kyle et al., report the production of self-assembling biomaterials for tissue engineering. Trends Biotechnol, 2009, 27(7):423-33. Other examples of hydrogel polypeptides are certain leucine zipper coiled-coil domains, EF-hand domains, and elastin-like polypeptides. See also Banta et al., Annu Rev. Biomed. Eng., 2010, 12:167-86.

As used herein, the term "stem cell" refers to an "undifferentiated" cell capable of proliferation, self-maintenance, production of a differentiated cell or regeneration of a stem cell may be tissue. In preferred embodiments of the present disclosure, a stem cell is capable of differentiating into a differentiated myocardial cell, such as a cardiomyocyte.

The term "cardiac stem cell" refers to stem cells that are capable of differentiating into a cardiomyocyte. The term "cardiomyocyte" refers to any cell in the cardiac myocyte lineage that shows at least one phenotypic characteristic of a cardiac muscle cell. Such phenotypic characteristics can include expression of cardiac proteins, such as cardiac sarcomeric or myofibrillar proteins or atrial natriuretic factor, or electrophysiological characteristics.

As used herein, the term "progenitor cell" refers to a cell that is an undifferentiated cell that is capable of differentiating. One of skill in the art realizes that a progenitor cell is an ancestor cell to progeny descendant cells.

The term "autologous" refers to tissue, cells or stem cells that are derived from the same subject's body.

As used herein, the term "cell surface marker" refers to a protein, glycoprotein or other molecule expressed on the surface of a cell, which serves to identify the cell. A cell surface marker can generally be detected by conventional methods, for example, but not limited to immunohistochemistry, fluorescence activated cell sorting (FACS), or an enzymatic analysis.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include non-natural peptides, recombinant peptides, synthetic peptides, or a combination thereof.

The term "recombinant polypeptide" as used herein is defined as a polypeptide produced by using recombinant nucleic acids. The term "recombinant nucleic acid" as used herein is defined as a nucleic acid, e.g., DNA, produced by joining pieces from different sources.

The terms "variant" when used in reference to a polypeptide refer to an amino acid sequence that differs by one or more amino acids from another, usually related polypeptide.

The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

Sequence "identity" refers to the number of exactly matching amino acids (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "nucleic acid sequence" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The terms "a nucleic acid sequence encoding" a specified polypeptide refer to a nucleic acid sequence comprising the coding region of a gene or in other words the nucleic acid sequence which encodes a product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region if needed to permit proper initiation of transcription and/or correct processing of the primary RNA transcript. Alternatively, the coding region utilized in the expression vectors may contain endogenous enhancers, exogenous promoters, splice junctions, intervening sequences, polyadenylation signals, etc., or a combination of both endogenous and exogenous control elements.

The terms "in operable combination," "in operable order," and "operably linked" refer to the linkage of nucleic acid sequences in such a manner that a nucleic acid molecule capable of directing the transcription of a given gene and/or the synthesis of a desired RNA or protein molecule is produced. Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

The term "expression" when used in reference to a nucleic acid sequence refers to the process of converting genetic information encoded in a gene into RNA (e.g., mRNA, rRNA, tRNA, shRNA, or miRNA) through "transcription" of the gene (i.e., via the enzymatic action of an RNA polymerase), and into protein where applicable (as when a gene encodes a protein), through "translation" of mRNA.

"Expression vector" refers to a vector comprising a recombinant nucleic acid comprising expression control sequences operatively linked to a nucleotide sequence to be expressed. An expression vector comprises sufficient cis-acting elements for expression in an expression system; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant nucleic acid.

Methods of introducing and expressing genes and producing and isolating polypeptides associated with the genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a nucleic acid into a host cell include calcium phosphate precipitation, lipofection, particle bombardment, microinjection, electroporation, and the like.

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape.

Regardless of the method used to introduce exogenous nucleic acids into a host cell or otherwise expose a cell to the nucleic acid, in order to confirm the presence of the recombinant DNA sequence in the host cell, a variety of assays may be performed. Such assays include, for example, "molecular biological" assays well known to those of skill in the art, such as Southern and Northern blotting, reverse transcription polymerase chain reaction (RT-PCR) and PCR; "biochemical" assays, such as detecting the presence or absence of a particular peptide, e.g., by immunological means (ELISAs and Western blots).

Cell-free translation systems are commercially available and many different types and systems are well-known. Examples of cell-free systems include prokaryotic lysates such as *Escherichia coli* lysates, and eukaryotic lysates such as wheat germ extracts, insect cell lysates, rabbit reticulocyte lysates, frog oocyte lysates and human cell lysates. Eukaryotic extracts or lysates may be preferred when the resulting protein is glycosylated, phosphorylated or otherwise modified. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1), IF-2, IF-3, elongation factor T (EF-Tu), or termination factors.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

The term "subject" may encompass any vertebrate including but not limited to humans, mammals, reptiles, amphibians and fish. However, advantageously, the subject is a mammal such as a human, or other mammals such as a domesticated mammal, i.e., dog, cat, horse, and the like, or production mammal, i.e., cow, sheep, pig, and the like.

The term "therapeutically effective amount" as used herein refers to an amount that results in an improvement or remediation of the symptoms of the disease or condition.

As used herein, the term "cardiovascular disease or disorder" refers to disease and disorders related to the cardiovascular or circulatory system. Cardiovascular disease and/or disorders include, but are not limited to, diseases and/or disorders of the pericardium (i.e., pericardium), heart valves (i.e., incompetent valves, stenosed valves, Rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids). Yet further, one skill in the art recognizes that cardiovascular diseases and/or disorders can result from congenital defects, genetic defects, environmental influences (i.e., dietary influences, lifestyle, stress, etc.), and other defects or influences.

As used herein, the term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

Modulation of Cardiac Progenitor Cell Function by Hydrogel-dependent Notch1 Activation Cardiac progenitor cells (CPCs) can be obtained from autologous sources and have shown promising outcomes in Phase I trials in patients with cardiovascular disease. However, lack of both myocardial cell retention and specific soluble cues impedes successful regeneration. Thus, hydrogels that mimic cardiac-tissue could provide appropriate mechanical and chemical cues to augment CPC function. Stem cell function is regulated by mechanical stimuli such as substrate stiffness, rigidity, shear stress, stretch and topography. Substrate stiffness depending on correlation with native tissue stiffness has been shown to regulate lineage specification of adult stem cells into lineages, endothelial differentiation of cardiac precursor cells and human pluripotent stem cell derived cardiomyocyte contraction. These studies elucidate control of stem cell fate and function through mechanical properties of culture environment.

In certain embodiments, the disclosure relates to hydrogels comprised of self-assembling peptide compositions. The hydrogel may be used as a platform for delivery or presentation pro-growth or pro-repair molecules, such as Notch receptors and ligands. Notch signaling is a conserved signaling pathway present in most cells and organisms. Notch proteins are a family of transmembrane proteins with differing ligands that play roles in the communication between adjacent cells (signaling) and development (differentiation & cell fate determination). Many of the ligands for the Notch proteins are also transmembrane proteins and thus signaling generally occurs through contact between cells.

Notch1 activation is dependent on physical properties of the hydrogel, which differentially regulates cardiogenic gene expression in CPCs, and that delivery of CPCs in 2RJ hydrogels improves acute myocardial retention and hemodynamic function after MI. Intramyocardial injection of CPCs in 2RJ hydrogels could be an efficient and robust cell delivery strategy for myocardial repair. As cKit+ CPCs can be isolated from cardiac biopsies even from patients with advanced heart failure, the improvement in cardiac function, contractility and retention in the CPC in 2RJ group could translate into positive clinical outcomes in patients.

Notch 1 is a receptor which features multiple extracellular EGF domains that traverses the membrane. One ligand for Notch 1 is Jagged 1 (JAG-1). Jagged 1 signaling is important to the development of the cardiovascular system, as mutations in Jagged 1 lead to cardiovascular related birth defects.

One method for improving reparative cellular heart therapies uses transplanted progenitor cells that are placed into a damaged area to repair the heart tissue in cases of heart disease or cardiovascular failure. Disclosed herein are self-assembling peptides that form hydrogels when combined with water. These hydrogel are used as a scaffold for supporting or growing cells, e.g., stem or precursor cells for therapy. Although, it is not intended that embodiments of the disclosure be limited by any particular mechanism, it is believed that these peptides form stable B-sheets and subsequently nanofibers under physiological pH and osmolarity conditions. In one embodiment, the peptide is combination of two sequences (a repeating RADA sequence and 20 amino acid JAG-1 sequence that mimics Jagged 1 signaling) connected by a polyglycine amino acid linker. When mixed with cardiac progenitor cells this peptide elicits expression of genes characteristic of cardiac cells.

As RADA16-II has no known cell adhesion motifs, physical entrapment of implanted cells within the hydrogel and the cell synthesized extracellular matrix are potential explanations for cell retention. The low immunogenicity and ability to incorporate bioactive motifs (such as RJ) within the self-assembling peptide (SAP) hydrogels provides a desirable platform.

In CHO cells with Notch-responsive YFP expression, increase in hydrogel concentration (1-3% w/v) in absence of ligand augmented Notch1 activation. This indicates that physical properties of the hydrogel depend on concentration. Stiffness and hydrogel porosity can affect Notch1 activation in 3D. High concentration hydrogels could lead to stiffness increases that saturate Notch1 signaling. Further, comparison of gene expression changes between CPCs in hydrogels of increasing concentration in absence of ligand (1R and 2R hydrogels) indicates increased activation of Notch responsive genes and certain other signal transduction mediators.

In vitro 3D culture of CPCs in RJ containing 1 or 2% hydrogels increased expression of Hey1, a downstream target of Notch1. Interestingly, culture on lower stiffness 1RJ hydrogels resulted in increased endothelial and smooth muscle gene expression. However, higher stiffness 2RJ hydrogels promoted cardiac gene expression indicating that the synergistic effect of hydrogel stiffness and Notch1 activation on cardiogenic gene expression could pre-commit CPCs towards the endothelial/smooth muscle or cardiac lineage respectively before in vivo delivery. Delivery of CPCs in 2RJ hydrogel provides an environment amenable to remodeling and repair.

To determine potential cell signaling pathways apart from Notch1 that are regulated by increasing concentration of the hydrogel (1R vs. 2R), a qPCR array was performed. CPCs cultured in lower concentration hydrogel (1R) had increased expression of proinflammatory genes such as TNFα, TRAIL and IFNγ. Increased Hey1 and Hes5 support the observed increase in its downstream target smooth muscle genes. The increase in TNFα along with higher levels of PDGF in CdM from 1RJ hydrogels could support the increased endothelial gene expression in CPCs in 1% hydrogels. MMP7 is increased in CPCs in 1R hydrogels and fibronectin which has been shown to be essential for reparative function of CPCs following infarction is a myocardial target of MMP7. Hence, increased MMP7 could degrade the CPC environment. The proinflammatory environment makes the low concentration hydrogels unfavorable for progenitor cell delivery in vivo.

Culture of CPCs in higher concentration 2R hydrogel increased expression of Hes1 and its downstream target Jagged1. Hence, increasing hydrogel concentration promotes ligand expression that could sustain Notch1 activation. Increase in Herpud1 which is known to interact with presenilins, a component of the γ-secretase complex could also enhance Notch1 activation. Moreover, increased expression of long chain acyl-CoA synthetases, BMP2 and TGFβ related genes that are known to exert beneficial effects on cardiomyogenesis combined with the cardioprotective effects of antioxidant genes, M-CSF and Wnt5A may improve function of CPCs delivered in 2R hydrogels and provides the basis for in vivo utilization. Presence of RJ could further enhance CPC survival, promote cardiac gene expression, and function.

A rat model of myocardial infarction (MI) was examined. Delivery of CPCs in 2RJ hydrogels led to sustained retention of implanted CPCs (~80%) in the myocardium for 1 week. Such high level of acute retention is significant as Terrovitis et al. report less than 20% retention of transplanted cardiac derived stem cells 1 week after administration in a rat model of MI. See Circ Res, 106 (2010), pp. 479-494. As low myocardial retention of implanted stem cells impedes cardiac regeneration and repair, delivery in 2RJ hydrogels provides an environment for successful CPC engraftment. Pressure-volume hemodynamic assessment of metrics indicative of functional improvement such as ejection fraction, stroke work and end systolic volume indicated preferential improvement in rats treated with CPCs in 2RJ hydrogels.

Cells

In certain embodiments, the disclosure relates to hydrogels prepared from the self-assembling peptides disclosed herein further comprising cells. In certain embodiments, the cells are stem or progenitor cell preparations, such as cKit positive cells, Sca1 positive cells, Flk positive cells, CD31 positive cells, CD34 positive cells, CD133 positive cells, CD34 positive hematopoietic stem cells, human umbilical cord blood-derived CD34 positive cells, human umbilical cord-derived mesenchymal stem cells (hUC-MSCs), CD34 and CD133 positive cells, Sca1 positive and CD31 positive cells, and combinations thereof inside or on the surface of the hydrogels.

In certain embodiments, cells in hydrogels disclosed herein are CD34 positive stem cells, CD133 positive bone marrow derived stem cells, adipose tissue derived stem cells, Bone marrow derived stem cells, or those reported by the following references.

Genead et al., report Islet-1 positive cells are cardiac progenitors. Stem Cells Dev. 2010;19:1601-1615.

Smith et al. report the regenerative potential of cardiosphere-derived cells expanded from percutaneous endomyocardial biopsy specimens. Circulation, 2007, 115:896-908

Messina et al. report cardiosphere-derived cardiac cells (CDC) can be clonally expanded from human myocardial biopsies and form cardiospheres, which express Sca-1, c-kit, Flk and CD31. Circ Res. 2004, 95:911-921. In certain embodiments, the disclosure contemplates human heart explants that generate a layer of cells and transferring these cells on or in hydrogels disclosed herein under conditions to replicate.

Liang et al. report proliferation, differentiation and migration of cardiac endothelial progenitor cells (Scalpositive/CD31 positive side-population cells). J Thromb Haemost, 2011, 9(8):1628-37.

Kim et al. report CD31 positive cells represent highly angiogenic and vasculogenic cells in bone marrow. Circ Res., 2010, 107(5):602-14.

Kim et al. report human peripheral blood-derived CD31+ cells have robust angiogenic and vasculogenic properties and are effective for treating ischemic vascular disease. J Am Coll Cardiol, 2010, 56(7):593-607.

Wang et al. report a role of the Sca1 positive/CD31 negative cardiac progenitor cell population in postinfarction left ventricular remodeling. Stem Cells, 2006, 24(7):1779-88.

Kawamoto et al. report CD34-positive cells exhibit increased potency and safety for therapeutic neovascularization after myocardial infarction compared with total mononuclear cells. Circulation, 2006, 114(20):2163-2169.

Agbulut et al. report comparison of human skeletal myoblasts and bone marrow-derived CD133 positive progenitors for the repair of infarcted myocardium. Journal of the American College of Cardiology, 2004, 44(2):458-463.

In certain embodiments, the other cells, e.g., stem and progenitor cells are isolated by markers such as SSEA-1, Oct-3/4, Is1-1, cKit (CD117, SCFR), Sca-1(Ly 6), MDR-1 (Abcbl, Pgp), Abcg2(MXR1, BCRP), CD133(prominin), CD90(Thy-1), CD105(endoglin), CD34, CD31(PECAM-1), CD45(LCA), VEGFR2 (KDR, Flk-1), and combinations thereof. Other cells contemplated for isolation are those the express bone morphogenetic protein receptor (BMPR), CD34, CD34+Sca1+Lin-profile, CD38, CD44, fibroblast colony-forming unit (CFU-F), Muc-18 (CD146), stro-1 antigen, B-1 integrin, O4, O1, cytokeratin 19 (CK19), cluster of designation 30 (CD30), neuronal cell-adhesion molecule (N-CAM), stage-specific embryonic antigen-3 (SSEA-3), stage-specific embryonic antigen-4 (SSEA-4), stem cell factor (SCF or cKit ligand).

In certain embodiments, the cells have the potential to develop into different cell types in the body during growth. In certain embodiments, the cells have the potential to become another type of cell with a more specialized function. In certain embodiments, the cells are capable of renewing themselves through cell division. In certain embodiments, the cells can be induced to become tissue- or organ-specific cells with special functions such as the heart, lung, skin, muscle, bone, cartilage, and fibrous connective tissue or brain. In certain embodiments, the cells are mesenchymal stem cell to produce bone cells (osteocytes), cartilage cells (chondrocytes), and connective tissue such as tendons. In certain embodiments, the cells are neural stem cells to produce nerve cells (neurons) astrocytes, and oligodendrocytes. In certain embodiments, the cells are epithelial stem cells to produce absorptive cells, goblet cells, and enteroendocrine cells. In certain embodiments, the cells are skin stem cells to produce keratinocytes.

In certain embodiments, the cells are embryonic stem cells, human embryonic stem cells, and/or non-embryonic somatic or adult stem cells. In certain embodiments, the cells are induced pluripotent stem cells (iPSCs).

In certain embodiments, the cells are stem cells that are capable of differentiating into a cardiomyocyte cell have "cardiomyocyte potential". Cardiomyocyte potential refers to the ability to give rise to progeny that can differentiate into a cardiomyocyte under specific conditions. Examples of stem cells with cardiomyocyte potential include pluripotent cells, progenitor cells (i.e., circulating endothelial progenitor cells or hemangioblasts), stem cells (i.e., hematopoietic stem cells, embryonic stem cells, or fibroblasts (i.e., muscle fibroblast, cardiac fibroblast, etc.). Stem cells can be isolated from embryonic or nonembryonic donors. The tissues from which the stem cells can be isolated include, for example, but are not limited to the bone marrow, the spleen, the liver, peripheral blood, umbilical cord tissue, umbilical cord blood, adipose tissue or skin. The stem cells are isolated using standard techniques well known and used in the art, for example, but not limited to those described in U.S. Patent Application No. US20020142457, U.S. Patent Application No. US20030082153

The donor tissue or sample can be isolated from a vertebrate, more particularly a mammal, for example, human, dog, cat, monkey, mouse, rat, bird, etc. More preferably the mammal is an adult mammal. In preferred embodiments, the mammal is a human. The tissue and/or sample can include the entire tissue or sample, a portion of a tissue or sample, or biopsy sample.

In certain embodiments, the cells are cardiac stem cells isolated from heart tissue, thus cardiac-derived stem cells. The heart tissue can be isolated from a vertebrate, more particularly a mammal. More preferably the mammal is an adult mammal. The tissue can include the entire heart, a portion of a heart, or biopsy sample.

Any method of isolating cells is acceptable, including affinity-based interactions, affinity panning, or flow cytometry. In preferred embodiments, flow cytometry is used to determine the fraction of cells that are the "cardiac stem cell" fraction. Flow cytometry involves the separation of cells or other particles in a liquid sample. Generally, the purpose of flow cytometry is to analyze the separated particles for one or more characteristics thereof. The basic steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Not only can cell analysis be performed by flow cytometry, but cell sorting can also be performed. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent tagged antibodies, which are used to mark one or more cell types for separation.

In certain embodiments, the cells are cardiac stem cells that express transcription factors that are necessary for cardiac development. The transcription factors can include one or more, but are not limited to GATA-4, MEF-2C, *TEF*-1, MLP/CRP1, MLP/CRP2, Tie-2, SRF, or Ang 1. Yet further, the cardiac stem cells may express telomerase reverse transcriptase (TERT).

In certain embodiments, the cells can be identified and purified on the basis of markers expressed inside the cell, not just those outside the cell, if a hybrid gene is first put into the cell, encoding a readily assayable marker and controlled transcriptionally by regulatory elements from non-coding DNA sequences of the gene whose expression is to be denoted by the hybrid reporter. Examples of readily assayable markers include, but are not limited to (i) spontaneously fluorescent proteins such as green fluorescent protein, cyan fluorescent protein, yellow fluorescence protein, and red fluorescent protein; or (ii) surface proteins not expressed otherwise expressed by the cell receiving the marker gene. Examples of regulatory elements are promoters and enhancers.

In certain embodiments, the hydrogels disclosed herein may be used for enhancing differentiation of a cell, e.g., increasing the extent of the acquisition or possession of one or more characteristics or functions which differ from that of the original cell (i.e., cell specialization). This can be detected by screening for a change in the phenotype of the cell (i.e., identifying morphological changes in the cell and/or surface markers on the cell).

In certain embodiments, the hydrogels disclosed herein may be used to enhance conversion or differentiation of a stem cell into a cardiomyocyte cell includes the act of increasing the extent of the acquisition or possession of one or more characteristics or functions that are used to identify a cell as a cardiomyocyte. For example, a specific function can include spontaneous beating, however, the present invention is not limited to this function of spontaneous beating. Other functional properties include, but are not limited to cardiac differentiation in tissue culture in response to 5'azacytidine, to other inhibitors of DNA methylase or DNA methylation, or cardiac differentiation in tissue culture that is dependent on bone morphogenetic proteins (BMPs) or their receptors regardless of the instigating signal. The conversion of a stem cell into a cardiomyocyte cell includes enhancing factors that are known to be required to convert cells into cardiomyocytes for example, BMP or Wnt.

In certain embodiments, the hydrogels disclosed herein may be used in combination with other methods for inducing cardiomyocytes from stem cells having the potential to differentiate into cardiomyocytes, e.g., induction of differentiation by the treatment with a DNA-demethylating agent, induction of differentiation using a factor which is expressed in the cardiogenesis region of a fetus or a factor which controls differentiation into cardiomyocytes in the cardiogenesis stage of a fetus, and induction of differentiation using a culture supernatant of the cells having the potential to differentiate into cardiomyocytes or cardiomyocytes differentiated from the cells.

Methods of Use

In certain embodiments, the disclosure relates to methods of treating or preventing diseases or disorders comprising administering an effective amount of a composition comprising cells and/or hydrogels prepared by the processes disclosed herein to a subject in need thereof.

In certain embodiments, with regard to cardiac diseases or conditions, the composition is administered by injection into cardiac tissue or pericardium, and/or infusion into the circulatory system. In certain embodiments, the composition is administered by implanting a hydrogel disclosed herein in an area of the subject, e.g. within or adjacent to cardiac tissue or cells. In certain embodiments, administrative routes for treatments disclosed herein may be by intracoronary infusion; transendocardial and epicardial intramyocardial injection.

In certain embodiments, the cells are autologous. In certain embodiments, the disclosure relates to methods of treating or preventing diseases or disorders comprising isolating cells from a subject, contacting the cells with a hydrogel disclosed herein, optionally replicating the cells, and administering the cells back into the subject or implanting the hydrogel into a desired area of the subject.

In certain embodiments, the disclosure relates to a method of treating a subject suffering from a cardiovascular disease comprising the step of administering cells produced by processes disclosed herein. In certain embodiments, the cells are autologous, heterologous, or homologous, and the cells differentiate into at least one cardiac cell type selected from the group consisting of myocytes, endothelial cells, vascular smooth muscle cells, and fibroblasts.

In certain embodiments, the cardiovascular disease is selected from the group consisting of coronary artery disease, myocardial infarction, ischemic heart disease and heart failure. The cells are administered via a parenteral route, for example, intravenously, or via direct injection into the heart of the subject. The cells can also be contained in the gel or combined with a gel or other matrix and the gel or matrix is implanted into the subject.

In certain embodiments, the disclosure relates to a method of treating a subject suffering from an infarcted myocardium comprising the step of administering to the subject an effective amount of cells prepared by processes disclosed herein, wherein the amount repairs the infarcted myocardium. The repairs comprise regeneration of cardiomyocytes.

In certain embodiments, the disclosure relates to a method of targeting injured myocardium comprising the step of administering to the subject cells produced by processes disclosed herein, wherein the cells migrate and attach to the injured myocardium.

In certain embodiments, the disclosure relates to a method of repairing an injured myocardium comprising the step of administering to a subject an effective amount of cells made by processes disclosed herein, wherein the amount is effective in repairing the injured myocardium. Repairing the myocardium comprises at least partially restoring structural integrity or functional integrity to the injured myocardium.

In certain embodiments, the disclosure relates to a method of repairing injured coronary vessels comprising the step of administering to a subject an effective amount of cells made by processes disclosed herein, wherein the amount is effective in regenerating vascular cells to repair the vessels.

In certain embodiments, the disclosure relates to a method of generating myocytes comprising the steps of: obtaining cells disclosed herein and differentiating the cells to generate myocytes in hydrogels disclosed herein. The cells are further differentiated by the addition of a transcription factor for cardiac development, for example, Nkx2.5 into the gel.

In certain embodiments, the disclosure relates to a method of treating damaged myocardium in a subject comprising the steps of: obtaining autologous cells from the subject; proliferating the cells in hydrogels disclosed herein; and administering intravenously to the subject the cells, wherein the cells migrate to the damaged myocardium. The cells can be derived from blood, bone marrow, and/or a tissue biopsy from the subject.

In certain embodiments, methods disclosed herein may be used or administered in combination with other agents used to treat cardiovascular diseases or condition such as with antiplatelet agents (clopidogrel, etc.), glycoprotein IIb/IIIa inhibitors (tirofiban), antithrombins (lovenox, bivalirubin), or thrombolytics (t-PA).

In certain embodiments, methods disclosed herein may be used or administered in combination with other methods used for maintenance, prophylaxis, prevention of cardiovascular diseases or conditions, such as a heart attack such as beta-blockers, ACE inhibitors and angiotensin receptor blockers (Captopril, ramipril), and statins (Atorvastatin).

Pharmaceutical Compositions

In certain embodiments, the disclosure relates to a pharmaceutical composition comprising cells made by processes disclosed herein and a pharmaceutical carrier. The pharmaceutical compositions may be used to treat diseases or conditions, including, but not limited to, coronary heart disease, arteriosclerosis, ischemic heart disease, angina pectoris, myocardial infarction, congestive heart failure and other diseases of the arteries, arterioles and capillaries or related complaint. Accordingly, the disclosure involves the administration of cells produced herein as a treatment or prevention of any one or more of these conditions or other conditions involving weakness in the heart, as well as compositions for such treatment or prevention.

The pharmaceutical compositions disclosed herein may be administered via injection, including, but not limited to subcutaneous or parenteral including intravenous, intraarterial, intramuscular, intraperitoneal, intramyocardial, transendocardial, transepicardial, intranasal administration as well as intrathecal, and infusion techniques.

Solutions of the cells may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain an agent to prevent the growth of microorganisms. The pharmaceutical forms suitable for injectable use include sterile aqueous solutions (U.S. Pat. No. 5,466,468, specifically incorporated herein by reference in its entirety). The cells may be combined with the carrier in any convenient and practical manner, i.e., by solution, suspension, emulsification, admixture, encapsulation, absorption and the like. Such procedures are routine for those skilled in the art.

In a further embodiment of the present disclosure, cells produced herein are contained in or combined or mixed thoroughly with a solid or semi-solid carrier, e.g., hydrogel. Stabilizing agents can be also added in the mixing process in order to protect the composition from loss of therapeutic activity. Examples of stabilizers for use in the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. An example of a semi-solid or solid carrier includes a matrix or gel polymer or gel ointment in which the stem cells are combined resulting in a composition that can be used to graft the cells onto the myocardium of a subject.

EXAMPLES

A Self-assembling Peptide Hydrogel Composed of Alternating Hydrophilic and Hydrophobic Amino Acids Cell therapy for heart failure is typically limited by the lack of implanted cell retention in the infarcted heart. Several studies have utilized natural and synthetic polymers tethered with growth factors and biological small molecules for use in disease models. However, these approaches are limited by the processing technique involved in tethering or incorporating these proteins/peptides within the polymer which could affect the bioactivity of these proteins. This problem is circumvented by synthesizing peptide (JAG-1) as part of the self assembling peptide and does not require additional chemical processing during hydrogel formation. The use of the JAG-1-self assembling peptide hydrogel improves survival and retention of embedded cells as JAG-1 mediated Notch-1 activation promotes stem/progenitor cell survival and differentiation. In certain embodiments, the hydrogel may be used as a stem/progenitor cell vehicle to treat heart failure and other cardiovascular diseases wherein the hydrogel is composed of a self-assembling peptide containing JAG-1 to deliver cardiac stem/progenitor cells to the infarcted heart.

Beyond cardiac therapy, it is believed that this technology could be applied in a more platform-like manner by incorporating other peptides to repair cardiac or other tissues, depending upon the factors used.

With the peptide (R) of the sequence H2N-RARADA-DARARADADA-OH (SEQ ID NO: 2), self-assembling peptide hydrogels form in water as nanofibers at physiological pH and osmolarity. Typically, the nanofibers are 7-20 nm in diameter comprising greater than 99% water. The nanofiber scaffold is non-inflammatory and non-immunogenic and promotes cell-cell interactions. By solid-phase synthesis or recombinant technology, the scaffold can be modified with peptide ligands and adhesive motifs to provide signaling cues and promote cell retention in the scaffold.

JAG-1 (CDDYYYGFGCNKFCRPR)(SEQ ID NO: 1) can be incorporated into the self-assembling peptides to generate bioactive scaffolds with the potential to regulate Notch signaling in a ligand density dependent manner. The self-assembling sequence RADA (or R) (RARADADARA-RADADA)(SEQ ID NO: 2) with a 7 glycine linker following the terminal alanine is followed by the active sequence of the Notch ligand Jagged-1 (JAG-1) to create the fusion peptide (RJ). As a control, the JAG-1 portion may be replaced with the scrambled sequence (RCGPDCFD-NYGRYKYCF)(SEQ ID NO:4) (RS) with no known cell surface binding site can be used as a control to check for the specificity of JAG 1 in activating Notch-1 signaling. The fusions can be combined with R in a ratio of 1:10 to ensure the extra sequence does not interfere with nanofiber assembly. These peptide scaffolds self-assemble at physiological pH and osmolarity (in 295 mM sucrose solution) into nanofiber hydrogels. After synthesis, the peptides can be purified by high pressure liquid chromatography on reverse-phase columns. Purity can be assessed by HPLC and the presence of a correct composition by amino acid analysis.

The 20 amino acid long peptides JAG-1 and SCR-1 do not self-assemble at physiologic pH and osmolarity.

| Peptide | % w/v | Self-Assembly |
|---|---|---|
| R (RARADADARARADADA) | 1 | yes |
| RJ [RARADADARARADADA(G7)(JAG-1)] (SEQ ID NO: 5) | 1 | no |
| RS [RARADADARARADADA(G7)(SCR-1)] (SEQ ID NO: 6) | 1 | no |

However, when JAG-1 or SCR-1 are mixed with the peptide hydrogel R at a 1:10 ratio, the peptide self-assembles into a hydrogel. The self-assembling peptide (R) and the peptides with Jag-1 (RJ) or scrambled (RS) attached are weighed out to create hydrogels of 1-3% w/v, i.e., hydrogels with varying % concentration from 1 to 3% w/v peptide wherein R is combined with RJ or RS in a ratio of 1:10.

A sucrose solution (295 mM) is added to the peptides and sonicated. The RJ or RS peptide solutions are mixed with the R solution at 1:10 and allowed to form the hydrogel. The time required to form the hydrogel depends on the concentration of the gel. In certain embodiments, the disclosure relates to the synthesis of self assembling peptides which contain the active ligand JAG-1 attached to it. This enables easy dose manipulation of JAG-1 to achieve Notch-1 activation. Data indicates that RJ when mixed with cardiac progenitor cells elicits expression of genes characteristic of cardiac cells (as well as other cell types) compared to control (R) peptide linked to a nonfunctional peptide.

Figure 1B:
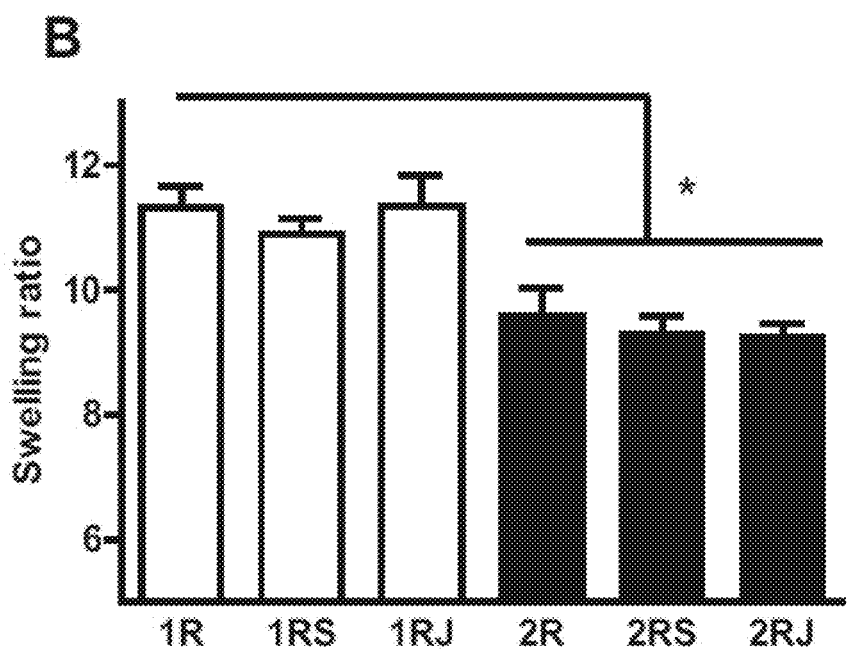
FIG. 1B shows data on the swelling ratio of the hydrogels determined at 24 h following gelation as in FIG. 1A. All the 1% hydrogels had a significantly higher swelling ratio than the corresponding 2% hydrogels.

Peptides have been created containing a ligand for Notch-1 activation that self assembles into a hydrogel. For determination of swelling ratio, the hydrogels were created in a 100 mL total volume and allowed to swell in 295 mM sucrose solution. After 24 h, the wet weight of the gels was measured. The gels were then lyophilized and the dry weight noted. Swelling ratio was calculated as the (wet weight–dry weight)/wet weight. Mechanical testing of hydrogel formulations by atomic force microscopy showed that addition of either scrambled (RS) or Jagged1 (RJ) peptide to the SAP did not alter the Young's modulus in comparison with unmodified hydrogels at both 1 and 2% w/v. The average Young's modulus for 1% and 2% hydrogels was 500 Pa and 1800 Pa respectively (FIG. 1A). The 1% hydrogels had a significantly higher swelling ratio than the corresponding 2% hydrogels indicating a more loosely linked peptide network at lower polymer density with no significant effect in network structure on addition of either RS or RJ peptide (n=3, p<0.05, FIG. 1B).

Notch1 Activation by Hydrogel

Figure 2A:
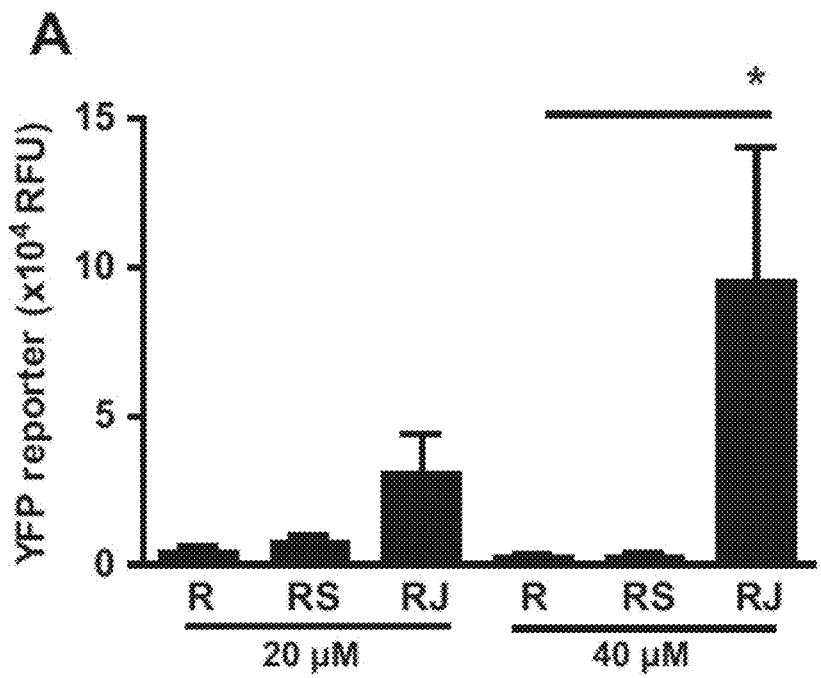
FIG. 2A shows data indication Notch1 activation in 3D is dependent on hydrogel concentration. CHO cells with Notch1 responsive YFP expression were cultured in 2D with media containing R, RS or RJ at 20 or 40 μm for 48 h. A significant increase in Notch1 activation was observed on treatment with 40 μm RJ.
Figure 2B:
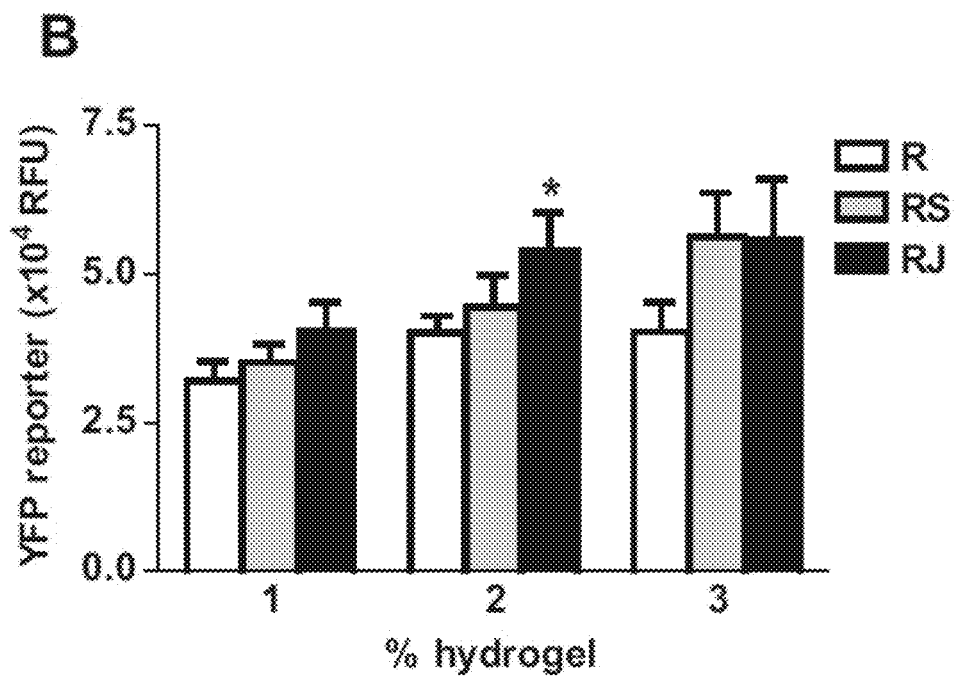
FIG. 2B shows results of experiments where CHO cells were cultured in 3D in 1-3% w/v hydrogels containing R, RS or RJ for 48 h. A significant increase in Notch1 activation was observed on increasing hydrogel concentration (open bars) and presence of RJ at 2% had the highest levels of Notch1 activation (middle black bar).

CHO cells with Notch1-responsive YFP expression were cultured in media containing 20 or 40 μm R, RS or RJ for 48 h. A significant increase in YFP expression was observed on treatment with RJ at 40 μm compared to all other treatment groups (p<0.05, n =3, FIG. 2A). These cells were also cultured in 3D in 1-3% w/v hydrogels composed of R, RS or RJ for 48 h. A significant increase in YFP expression was observed with increasing hydrogel concentration in absence of any ligand (n=7, p<0.01, open bars, FIG. 2B). Interestingly, presence of RJ in 2% hydrogels resulted in maximum Notch1 activation (p<0.05, middle black bar, FIG. 2B). Further increase to 3% w/v did not promote Notch1 activation.

In vitro Gene Expression

Cardiac progenitor cells (CPCs) were isolated from 2 month old male Sprague Dawley rats by digesting the heart with Collagenase followed by magnetic sorting for cKit positive cells. The CPCs were cultured on Ham's F12 supplemented with FBS, LIF, bFGF, L-Glutamine and antibiotics. Single cell cloning was performed by limiting dilution to obtain CPCs with >90% expression of cKit and the cardiac transcription factors nkx2-5 and gata-4. CPCs were cultured in self assembling hydrogels of various concentrations (1-3% w/v) with either empty, scrambled or JAG-1 peptide in 1:10 ratio for 48 hrs in Millicell Insets. qRT-PCRs were performed using Power SYBR green on the StepOne Plus Applied Biosystems machine. The Young's modulus of the hydrogels was determined using an MFP-3DBIO atomic force microscope (Asylum Research; Santa Barbara, Calif.), with a 4.74 μm diameter bead tippedsilicon nitride cantilever.

For cardiac progenitor cells, JAG-1 mediated Notch1 activation in 3D increases expression of the Notch1 target Hey1.

Figure 3A:
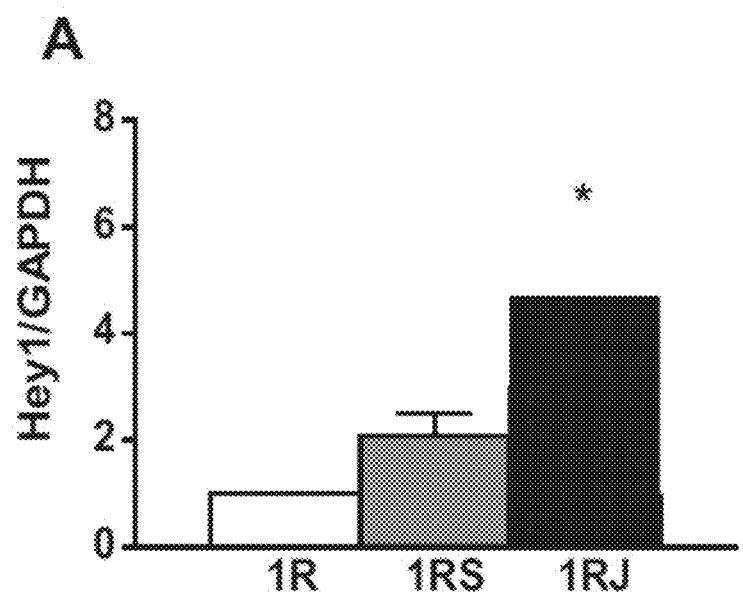
FIG. 3A shows data indicating the culture of CPCs in 1% hydrogels with RJ activates Notch1 signaling and promotes endothelial and smooth muscle gene expression. CPCs were cultured in 1% hydrogels (R, RS, RJ) for 48 h and expression of Notch-1 downstream target, Hey1 measured by qPCR.
Figure 3B:
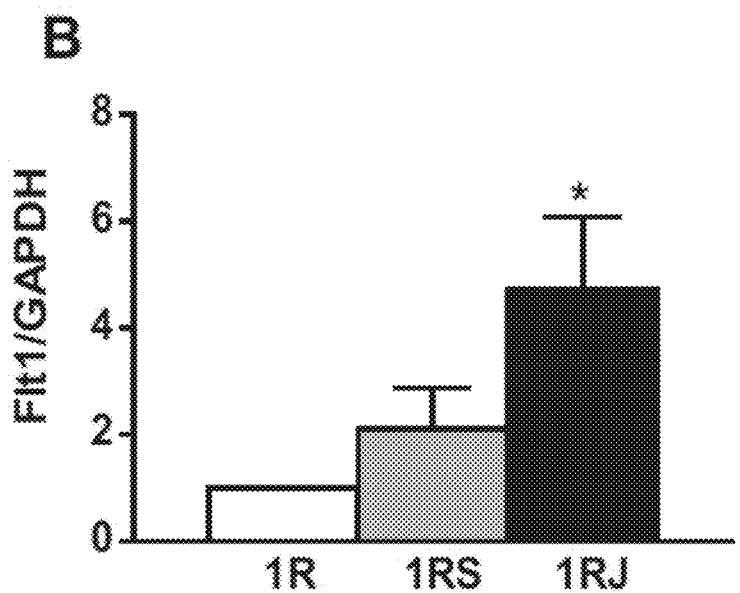
FIG. 3B shows data on expression of VEGF receptor1 Flt1 as in FIG. 3A.
Figure 3C:
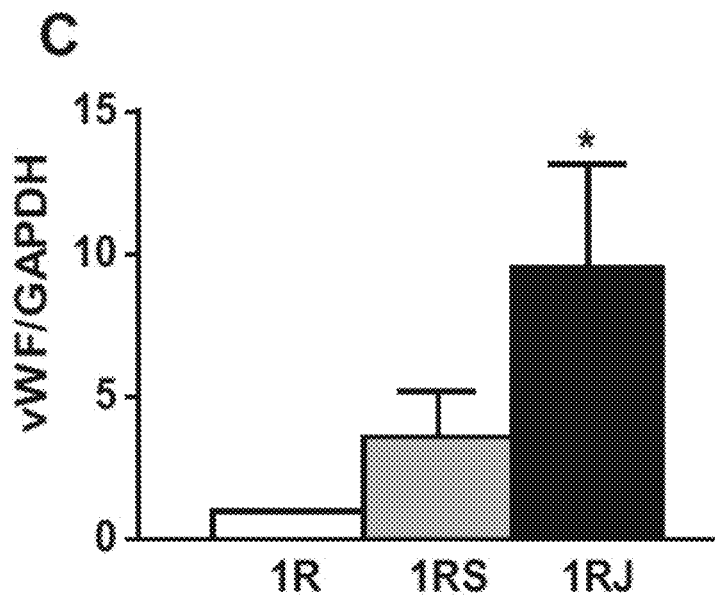
FIG. 3C shows data on expression of vWF as in FIG. 3A.
Figure 3D:
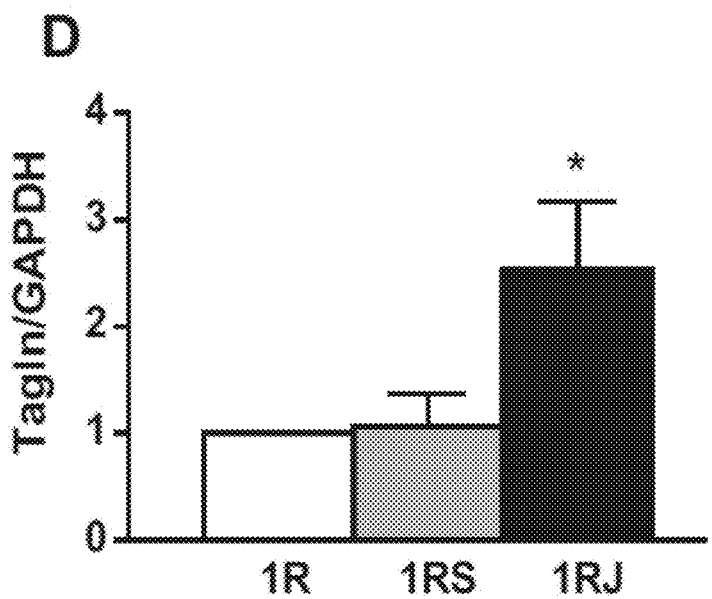
FIG. 3D shows data on expression of Tagln as in FIG. 3A.
Figure 3E:
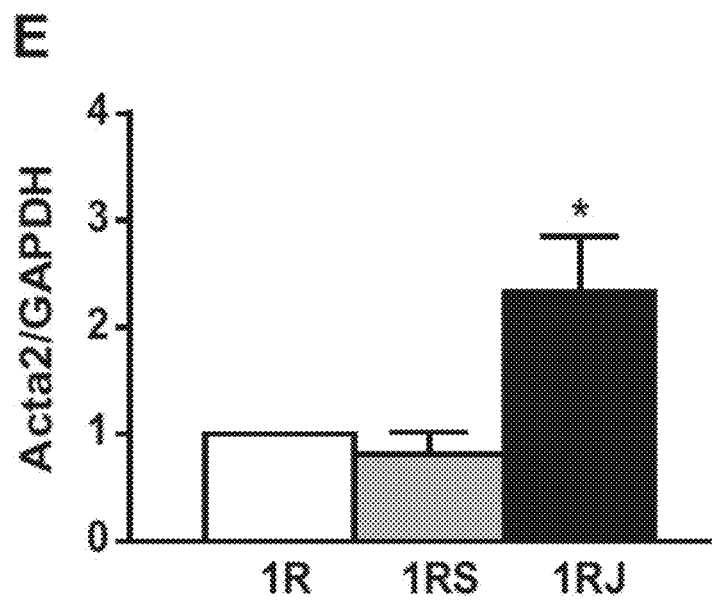
FIG. 3E shows data on expression of Acta2 as in FIG. 3A.

CPCs were clonally expanded and characterized to be >96% Notch1+, >90% c-Kit+, nkx2-5+(nk2 homeobox 5) and gata4+(GATA binding protein 4). CPCs were cultured in 1 or 2% (w/v) SAP hydrogels (1R, 1RS, 1RJ or 2R, 2RS, 2RJ) for 48 h. Culture in 1RJ hydrogels resulted in a significant increase in Hey1 (hairy/enhancer-of-split related with YRPW motif 1), a downstream target of Notch1 signaling (p<0.05, n=4; FIG. 3A). A significant increase in expression of the endothelial genes Flt1 (fms-related tyrosine kinase 1, p<0.05, n=5) and vWF (von Willebrand factor, p<0.05, n=8; FIGS. 3B and C), and the smooth muscle genes Tagln (Transgelin, p<0.05, n=7) and Acta2 (sm α-actin, p<0.05, n=7; FIGS. 3D and E) was observed with no change in expression of the cardiac genes, nkx2-5, Mef2c and Gata4.

Figure 4A:
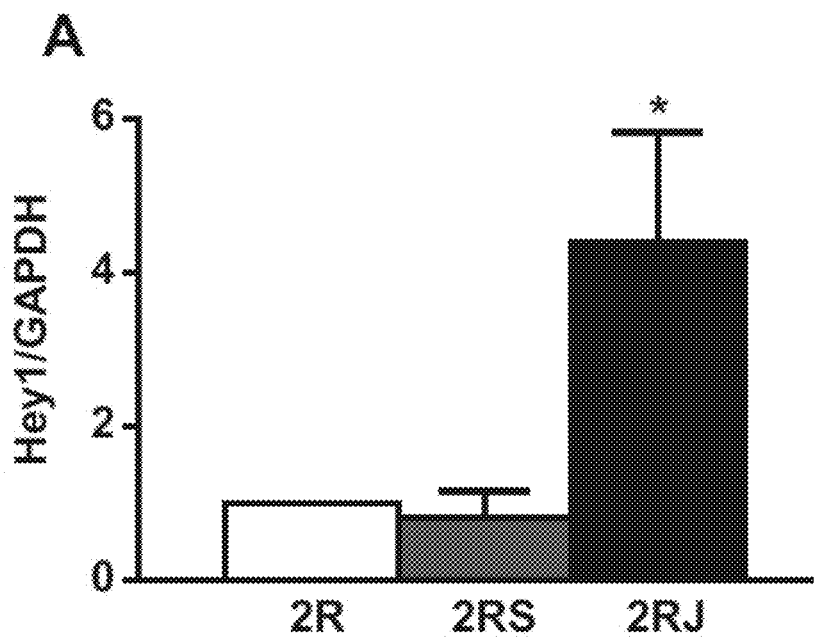
FIG. 4A shows data indicating the culture of CPCs in 2% hydrogels with RJ activates Notch1 signaling and promotes cardiac gene expression. CPCs were cultured in 2% hydrogels (R, RS, RJ) for 48 h and expression of Notch1 downstream target, Hey1, as measured by qPCR.
Figure 4B:
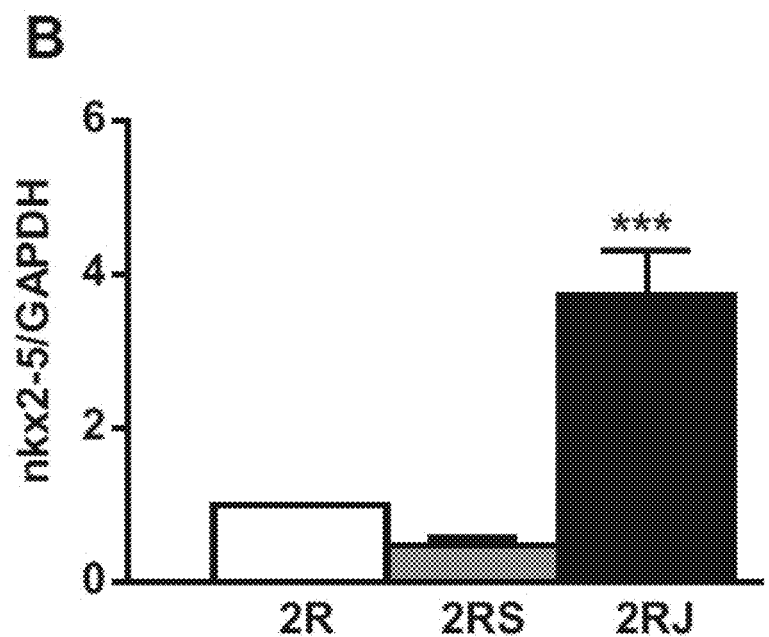
FIG. 4B shows data on expression of nkx2-5 as in FIG. 4A.
Figure 4C:
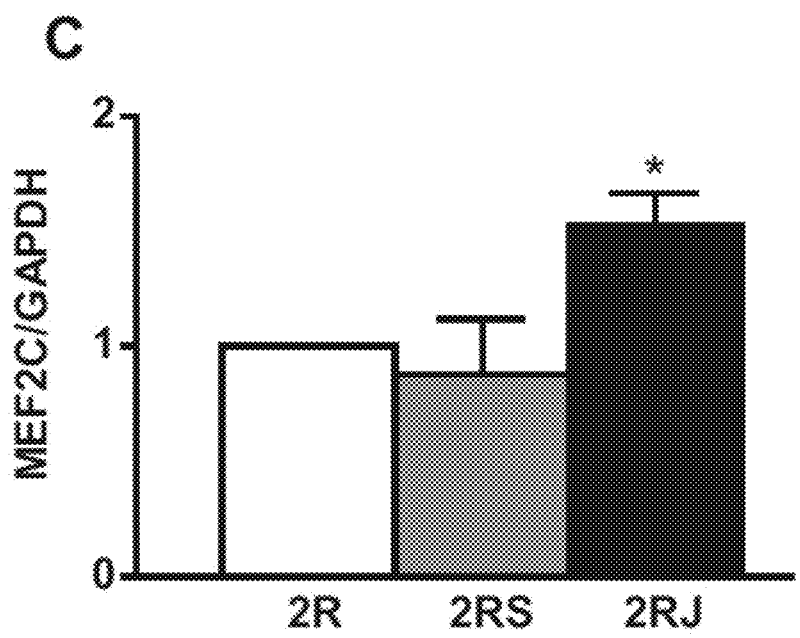
FIG. 4C shows data on expression of MEF2C as in FIG. 4A.
Figure 4D:
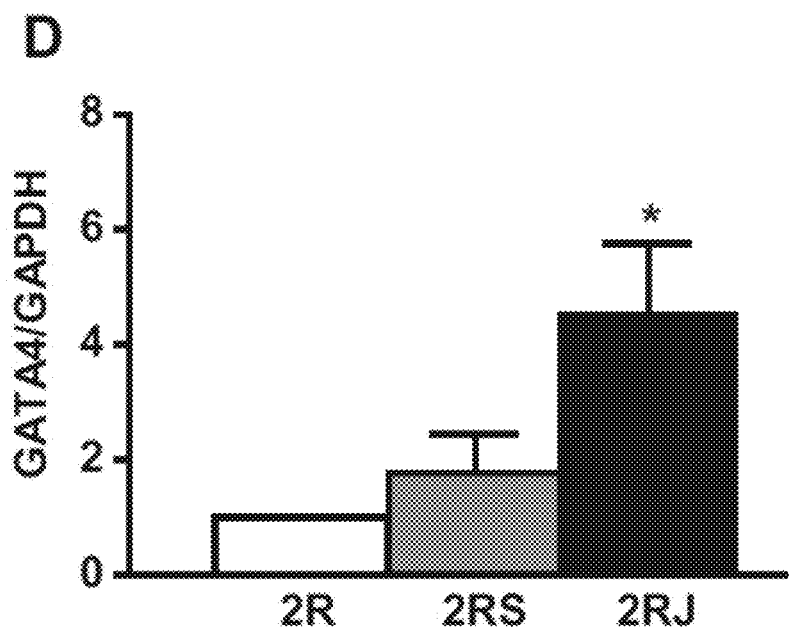
FIG. 4D shows data on expression of GATA4 as in FIG. 4A.

Culture of CPCs in 2RJ hydrogels increased expression of Hey1 (p<0.05, n=4, FIG. 4A) and promoted expression of the cardiac genes nkx2-5 (p<0.001, n=5), mef2c (p<0.05, n=8) and gata4 (p<0.05, n=6; FIG. 4B-D) with no changes in expression of the endothelial or smooth muscle genes. No significant differences were observed in gene expression between CPCs in control and scrambled hydrogels.

Figure 5A:
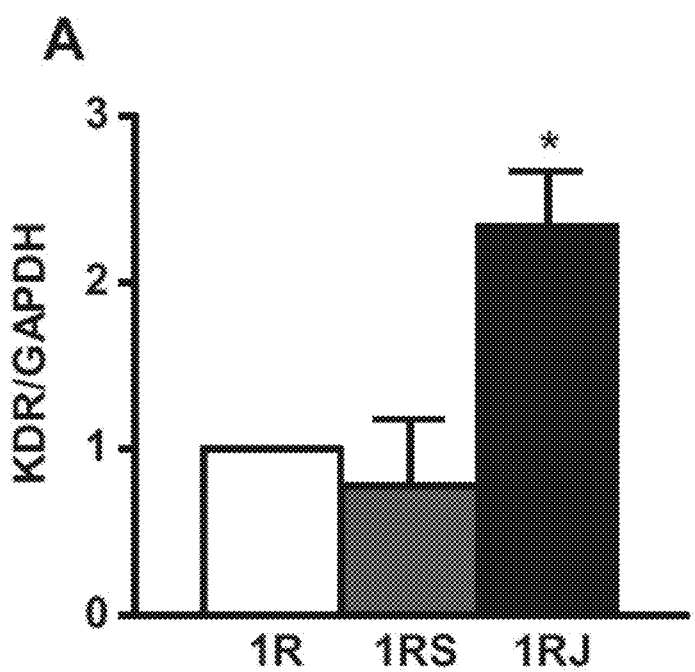
FIG. 5A shows data indicating the culture of mouse embryoid bodies in 1% hydrogels with RJ promotes endothelial and smooth muscle gene expression. Mouse EBs were cultured in 1% hydrogels (R, RS, RJ) for 1 week and expression of KDR as measured by qPCR.
Figure 5B:
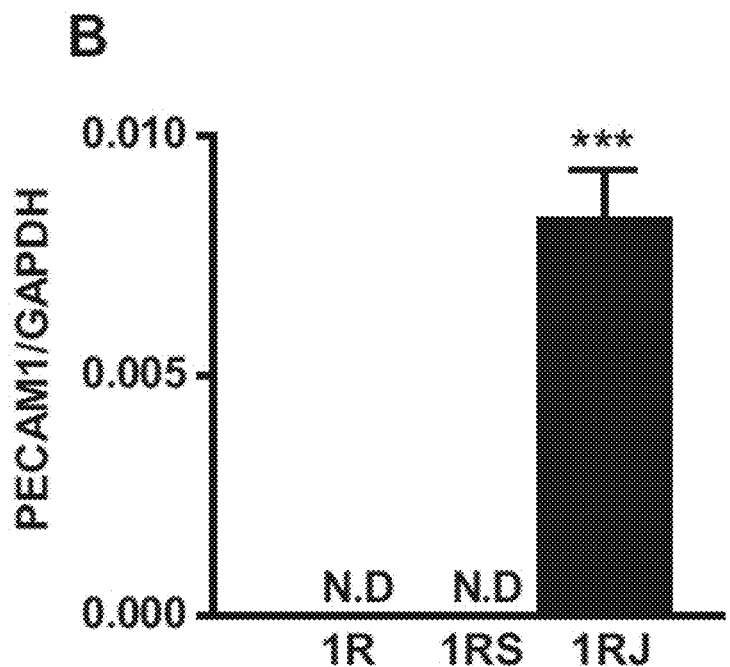
FIG. 5B shows data on expression of PECAM1 as in FIG. 5A.
Figure 5C:
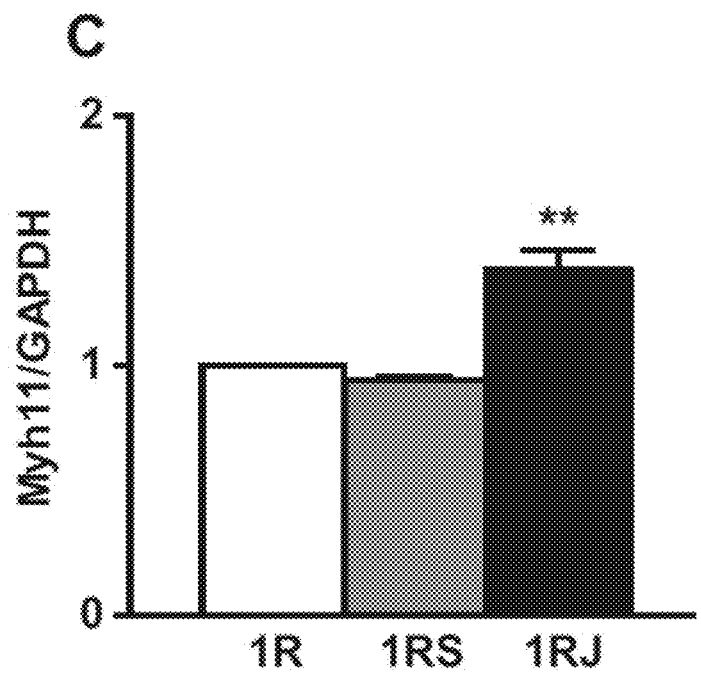
FIG. 5C shows data on expression of Myh11 as in FIG. 5A.

To determine if gene expression changes in response to hydrogel-mediated Notch1 activation were conserved between stem/progenitor cells, day 2 embryoid bodies (EBs) from mouse embryonic stem cells were cultured in low concentration (1%) hydrogels for 48 h. A significant increase in expression of endothelial and smooth muscle genes such as VEGF receptor KDR (Kinase insert domain receptor, p<0.05), PECAM1 (platelet/endothelial cell adhesion molecule 1, p<0.001) and Myh11 (smooth muscle myosin heavy chain, p<0.01) was observed in cells cultured in 1RJ hydrogels (n=3, FIG. 5A-C).

Expression levels of several signal transduction pathway targets in CPCs cultured in 1R or 2R hydrogels were analyzed by qPCR array. CPCs in 1R hydrogels had higher expression of proinflammatory genes such as TNFα, TRAIL and IFNγ, MMP7 and CyclinD2 compared to CPCs in 2R hydrogels. The downstream targets of Notch1-Hes5 and Hey1 were also increased indicative of Notch1 activation.

Culture of CPCs in higher concentration hydrogel (2R) resulted in increase of the Notch1 target Hes1, the Notch1 ligand Jagged1 and γ-secretase interacting gene Herpud1. Higher expression of i) antioxidant genes—glutathione reductase (Gsr), NAD(P)H dehydrogenase quinone 1 (Nqo1), Sequestosome 1 (Sqstm1) and carbonic anhydrase 9 (Car), ii) PPAR targets—Glut1, Fatty acid transporter member 4 (S1c27a4) and long chain acyl-CoA synthetases-members 4 and 5(Acsl4, Acsl5) iii) Bone morphogenetic protein 2 (BMP2), iv) Wnt ligands-Wnt5A and Wnt1 inducible signaling pathway protein 1 (Wisp1), v) TGFβ targets- Cyclin-dependent kinase inhibitor 1B (Cdkn1b) and epithelial membrane protein 1 (Emp1), vi) NFκB target macrophage colony stimulating factor 1 (M-CSF) and vii) JAK/STAT inhibitor-Suppressor of cytokine signaling 3 (Socs3) and JAK/STAT target myeloid cell leukemia sequence 1 (Mcl1) was detected.

Paracrine Effects of RJ Hydrogels

Conditioned media (CdM) was obtained from CPCs cultured for 48 h in 1R, 1RS, 1RJ, 2R, 2RS and 2RJ hydrogels. No change in levels of VEGF, GM-CSF, IP10, bFGF and IGF1 were observed between CPCs in 1R and 1RJ hydrogels. However, culture in 1RJ hydrogels increased expression of SCF, IL6 and PDGF.

CPCs cultured in 1RJ hydrogels had significantly increased platelet-derived growth factor-BB (PDGF) compared to 1R gels with levels below the limit of detection in CPCs in 2R and 2RJ hydrogels. Culture of rat cardiac endothelial cells (CECs) in 1RJ CdM led to more tubes and interconnections with a significant increase in tube length compared to 1R and 1RS CdM (n=3, p<0.05, representative images in right inset, FIG. 7B). ELISA for stem cell factor (SCF) in CdM showed a significant increase in 2RJ CdM. SCF binds to cKit on CPCs and is a chemoattractant for progenitor cell migration. CPC migration in a transwell Boyden chamber was significantly higher towards CdM from CPCs in 2RJ hydrogels compared to other group. As Notch1 signaling promotes cell proliferation, CPCs were cultured in 1R, 1RS, 1RJ, 2R, 2RS and 2RJ hydrogels for 24 h and cell proliferation was quantified as extent of EdU incorporated DNA in cells by click-iT EdU assay. CPCs cultured in 2RJ hydrogel had a significant increase in EdU incorporated DNA indicative of proliferation compared to all other groups. A significant increase in EdU incorporation was observed in primary adult cardiomyocytes cultured in 2RJ CdM indicative of proliferation. A similar result was observed in H9C2 myoblasts.

In vivo Cardiac Retention

Figure 6:
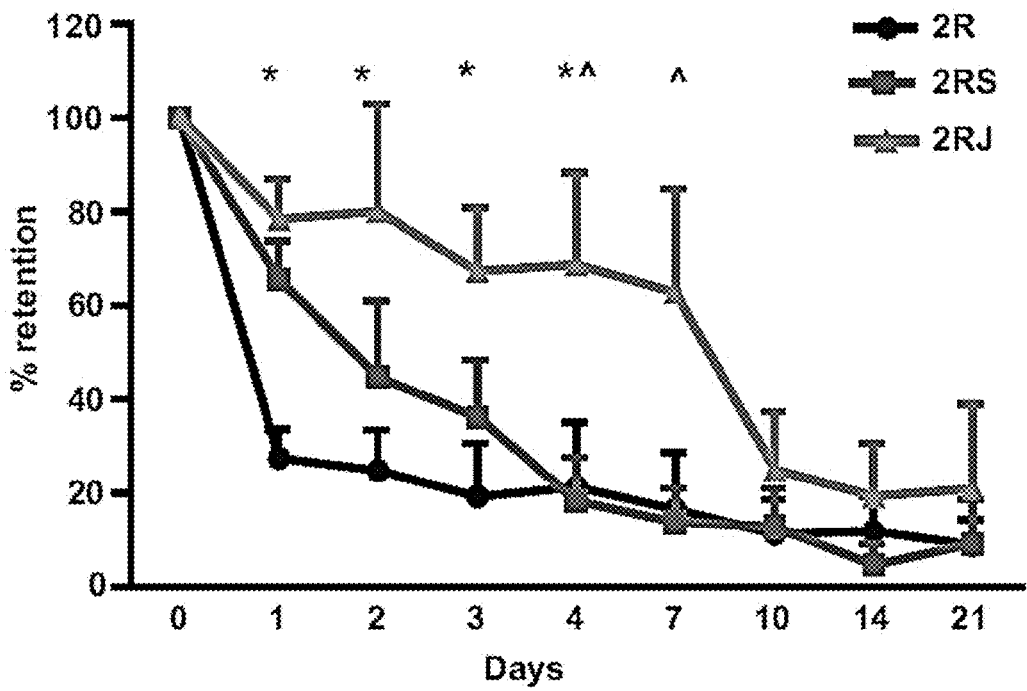
FIG. 6 shows data indicating improved myocardial retention of CPCs in 2RJ hydrogels. Rats with intramyocardial injection of DiR labeled CPCs were imaged on days 0, 1, 2, 3, 4, 7, 10, 14 and 21. Increased acute retention of implanted CPCs is observed in 2RJ hydrogels compared to CPCs in 2R and 2RS.

A rat model of myocardial infarction was used to determine the effect of CPC delivery in hydrogels. To analyze the extent of myocardial cell retention, DiR-labeled CPCs were injected in 2R, 2RS or 2RJ hydrogels in 3 areas around the infarct border zone. Time course fluorescent in vivo imaging of rats as a readout of cardiac retention showed that CPCs in 2RJ hydrogels had significantly higher % retention compared to CPCs in 2R and 2RS hydrogels until day 7 (FIG. 6).

In Vivo Cardiac Function

Figure 7:
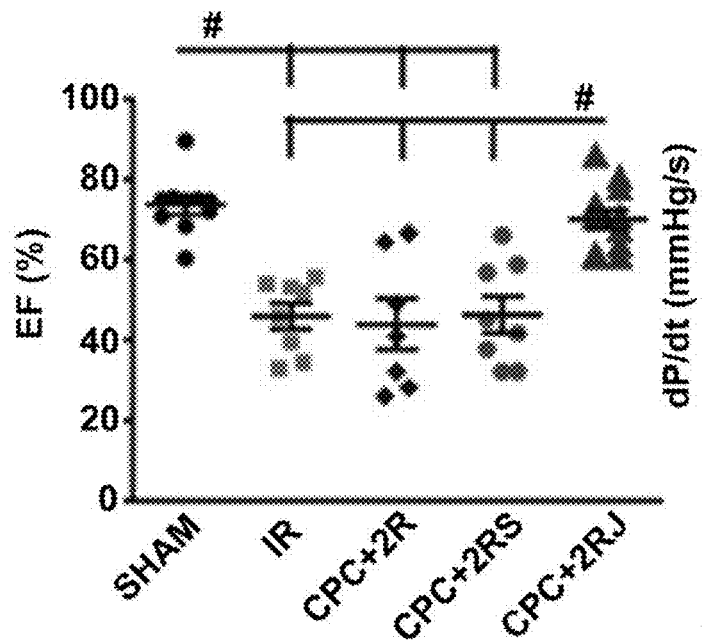
FIG. 7 shows data indicating CPCs in 2RJ hydrogels improve cardiac function and decrease fibrosis following MI. Pressure Volume Hemodynamic measurements and Pico-Sirius Red staining indicating ejection fraction (EF %) in rats treated with CPCs in 2RJ hydrogels.

The functional consequences of CPC implantation in 2R, 2RS or 2RJ hydrogels was investigated in rats subjected to 30 min of ischemic/reperfusion (IR). CPCs in 2R, 2RS, or 2RJ hydrogels were injected intramyocardially in 3 infarct border zone areas. Cardiac function was evaluated on day 21 by invasive pressure-volume hemodynamic measurements. IR significantly decreased ejection fraction of the hearts when compared to sham operated rats and treatment with CPCs in 2RJ hydrogels significantly improved ejection function comparable to sham operated rats (FIG. 7). No improvement in function was observed in rats treated with CPCs in empty (2R) or scrambled (2RS) hydrogels indicating the importance of 2RJ containing hydrogels in CPC mediated functional improvement following infarction. Treatment with CPCs in 2RJ hydrogels showed a trend for improvement in the cardiac contractility indicator ±dP/dt and significant improvement in end systolic volume. Among other parameters of ventricular function, the significant decrease in stroke work, stroke volume and cardiac output following IR was reversed in rats treated with CPCs in 2RJ hydrogels. No change in end diastolic volume was observed. Picosirius Red staining of heart sections demonstrated a significant increase in cardiac fibrosis in untreated infarcted hearts. In comparison, treatment with CPCs in 2RJ hydrogel resulted in a significant decrease in fibrosis.

The invention claimed is:

1. A hydrogel comprising a recombinant polypeptide in combination with a hydrogel polypeptide,
   wherein the recombinant polypeptide comprises a cell signaling sequence, wherein the cells signal sequence comprises SEQ ID NO: 1, fused to a hydrogel polypeptide sequence,
   wherein the hydrogel polypeptide and the recombinant polypeptide are in a ratio of between 1:5 to 1:15 by weight, and
   wherein the hydrogel polypeptide and the recombinant peptide are 1.5% to 2.5% by weight to volume of the hydrogel.

2. The hydrogel of claim 1 comprising a saccharide at a concentration of between 100 nm to 500 mM.

3. The hydrogel of claim 1 comprising a buffer creating a pH of between 7.0 to 7.7.

4. The hydrogel of claim 1, wherein the hydrogel further comprising a cardiac progenitor cell.

* * * * *